US012744114B2

(12) United States Patent
Hoffman

(10) Patent No.: US 12,744,114 B2
(45) Date of Patent: Sep. 22, 2026

(54) PHARMACEUTICAL ORDER PROCESSING SYSTEMS AND ASSOCIATED METHODS

(71) Applicant: Express Scripts Strategic Development, Inc., St. Louis, MO (US)

(72) Inventor: Robert E. Hoffman, Linden, IN (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 391 days.

(21) Appl. No.: 18/489,067

(22) Filed: Oct. 18, 2023

(65) Prior Publication Data

US 2025/0132006 A1 Apr. 24, 2025

(51) Int. Cl.
*A61J 1/03* (2023.01)
*G16H 10/60* (2018.01)
*G16H 20/13* (2018.01)
*G16H 40/67* (2018.01)

(52) U.S. Cl.
CPC ................ *G16H 20/13* (2018.01); *A61J 1/03* (2013.01); *G16H 10/60* (2018.01); *G16H 40/67* (2018.01)

(58) Field of Classification Search
CPC ........ G16H 20/13; G16H 10/60; G16H 40/67; A61J 1/03; B65B 5/02
See application file for complete search history.

(56) References Cited

U.S. PATENT DOCUMENTS 4,376,090 A * 3/1983 Marcus ................ B29C 49/064 264/537
6,962,715 B2 11/2005 Lee
7,386,965 B2 * 6/2008 McErlean ............ G06Q 10/087 53/135.2
8,392,020 B2 * 3/2013 Terzini .................... B65B 35/08 700/242
8,511,478 B2 8/2013 Terzini
9,240,093 B2 1/2016 Yuyama
9,567,119 B2 2/2017 Joplin
9,697,335 B2 7/2017 Joplin
10,695,902 B2 6/2020 Hoffman
10,723,497 B2 7/2020 Diaz Guerrero
10,730,653 B2 8/2020 Christopher
10,759,554 B2 9/2020 Sebastian
10,947,012 B1 3/2021 Johnson
11,424,016 B1 8/2022 Hoffman (Continued)

*Primary Examiner* — Patrick H Mackey
(74) *Attorney, Agent, or Firm* — Stinson LLP

(57) ABSTRACT

A pharmaceutical order processing system, components thereof, and associated methods. The pharmaceutical order processing system includes an order processing device, a container former, and a pharmaceutical dispensing device. The order processing device receives a pharmaceutical order of one or more pharmaceuticals and determines a container volume for containing at least a portion of the one or more pharmaceuticals based on the one or more pharmaceuticals. The container former is communicatively coupled to the order processing device. The container former forms a pharmaceutical container having the container volume determined by the order processing device. The pharmaceutical dispensing device is also communicatively coupled to the order processing device. The pharmaceutical dispensing device dispenses said at least a portion of the one or more pharmaceuticals into the pharmaceutical container formed by the container former.

20 Claims, 5 Drawing Sheets

(56) References Cited

U.S. PATENT DOCUMENTS

| | | | | |
|---|---|---|---|---|
| 12,503,259 | B2 * | 12/2025 | Colson | B65B 3/02 |
| 2011/0146835 | A1 * | 6/2011 | Terzini | G16H 70/40<br>141/98 |
| 2019/0163876 | A1 | 5/2019 | Remme | |
| 2021/0252658 | A1 * | 8/2021 | Gaffigan | B33Y 30/00 |
| 2022/0404818 | A1 * | 12/2022 | Stock | B41J 3/4073 |
| 2024/0336414 | A1 | 10/2024 | Hoffman | |

* cited by examiner

Order Processing Device
CPU
RAM
12
26
28
Pharmaceutical Dispensing Device
Pharmaceutical Counters
Pharmaceutical Stager
14
46
48
Labeling Device
34
Pharmaceutical Inspector
18
Container Sealer
20
Packager
24
Container Transporter
16
Container Former
Additive Manufacturing Machine
Thermoforming Machine
22
32
36

C
30B
30A
Name
Mon
30D
No.
Noon
30C
30E
Pharma
30

200
Receive Pharmaceutical Order
201
Determine Container Volume(s)
202
204
Form Pharmaceutical Container
206
Fill Pharmaceutical Container
208
Verify the Pharmaceutical(s)
214
210
Seal Pharmaceutical Container
212
Package Pharmaceutical Container

PHARMACEUTICAL ORDER PROCESSING SYSTEMS AND ASSOCIATED METHODS

FIELD

The present disclosure generally relates to processing pharmaceutical orders using pharmaceutical order processing systems, and more particularly to pharmaceutical order processing systems with pharmaceutical containers customized for each pharmaceutical order.

BACKGROUND

Pharmaceutical order processing systems process and fill a large number of prescriptions and prescriptions orders (e.g., pharmaceutical order) with pharmaceuticals. Pharmaceutical order processing systems typically involve labor intensive and/or complicated processes to sort and prepare portions of the pharmaceutical order such that the various portion of the pharmaceutical order may be correctly processed and/or joined up with other portions of the pharmaceutical order for packaging and shipment to the customer.

SUMMARY

In one aspect, a pharmaceutical order processing system comprises an order processing device configured to receive a pharmaceutical order including one or more pharmaceuticals. The order processing device is configured to determine a container volume for containing at least a portion of the one or more pharmaceuticals based on the one or more pharmaceuticals. A container former is communicatively coupled to the order processing device. The container former is configured to form a pharmaceutical container having the container volume determined by the order processing device. A pharmaceutical dispensing device is communicatively coupled to the order processing device. The pharmaceutical dispensing device is configured to dispense said at least a portion of the one or more pharmaceuticals into the pharmaceutical container formed by the container former.

In another aspect, a method of filling a pharmaceutical order including one or more pharmaceuticals comprises determining a container volume for containing at least a portion of the one or more pharmaceuticals based on the one or more pharmaceuticals, forming a pharmaceutical container having the determined container volume, and filling the formed pharmaceutical container with said at least a portion of the one or more pharmaceuticals.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
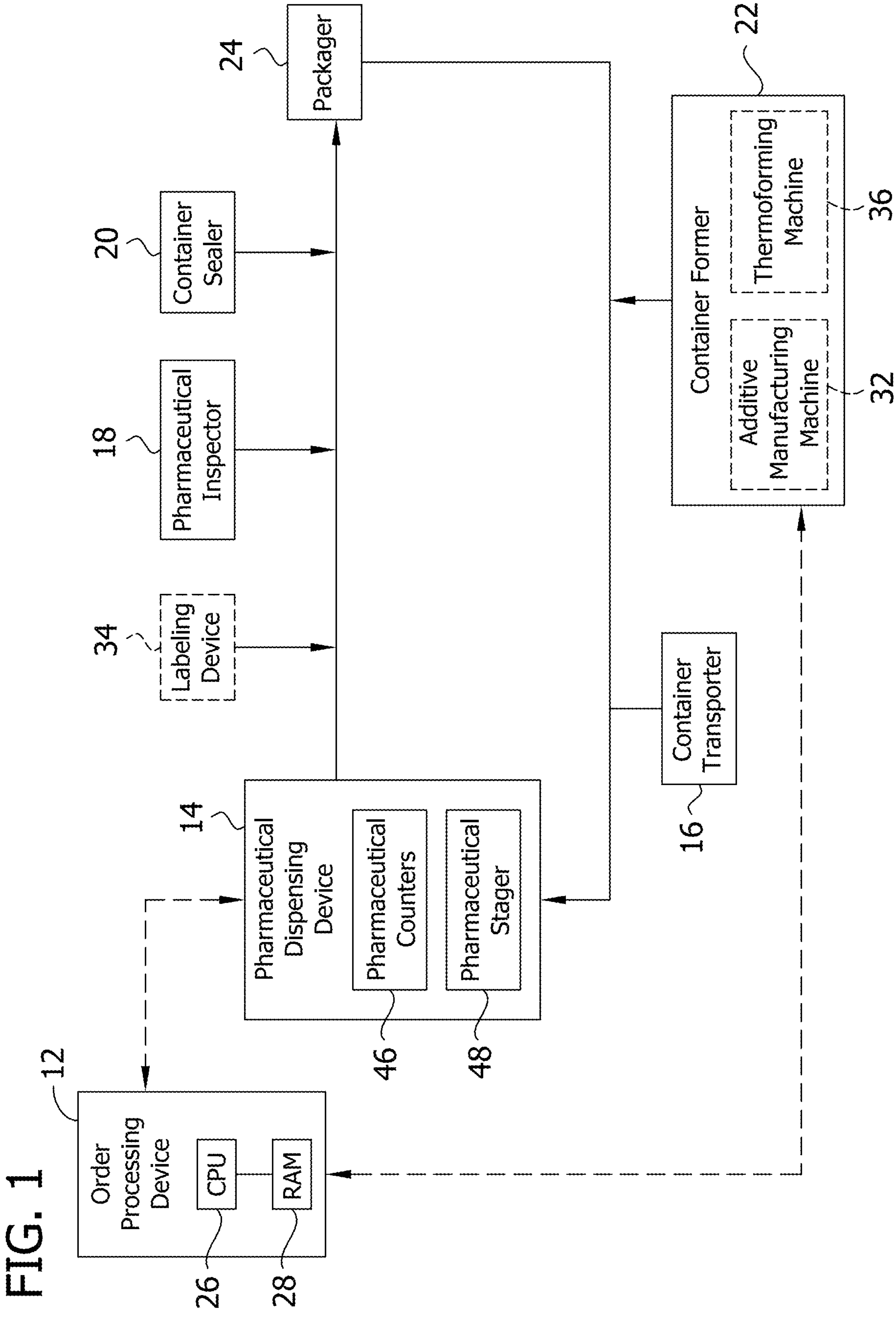
FIG. 1 is a schematic of a pharmaceutical order processing system according to one embodiment of the present disclosure.

The pharmaceutical order processing systems of the present disclosure process prescription or pharmaceutical orders, such as for a high-volume pharmacy. The pharmaceutical order generally embodies a pharmaceutical treatment regimen, typically prescribed by one or more doctors. The pharmaceutical order may include one or more pharmaceuticals (e.g., one or more types of pharmaceuticals). For example, the pharmaceutical order may include a single type of pharmaceutical (e.g., a single type of prescription drug) or may include two or more types of pharmaceuticals (e.g., two or more types of prescription drugs). The pharmaceuticals may be in the form of a pill, capsule, tablet, or the like.

In some embodiments, the pharmaceutical order processing systems of the present disclosure fill one or more pharmaceutical containers with exact counts of pharmaceuticals to fill the prescription order. In these embodiments, each container receives the same type of pharmaceutical and will receive a specific quantity (e.g., 30, 60, 90, etc.) of pharmaceuticals as designated by the pharmaceutical order. In this embodiment, each type of pharmaceutical is generally contained within one pharmaceutical container (e.g., type-based filling). Accordingly, the number of pharmaceutical containers for the pharmaceutical order generally corresponds to the number of different types of pharmaceuticals of the pharmaceutical order.

In some embodiments, the pharmaceutical order processing systems of the present disclosure are pharmaceutical dosing filler systems for filling pharmaceuticals orders with pharmaceuticals used in multi-drug treatment regimens or dose unit pharmaceutical orders. Dose unit pharmaceutical orders may include multiple separate dose unit containers, each containing multiple pharmaceuticals to be taken by the customer at the same time. Many patients take pharmaceutical treatments that involve several different pharmaceuticals (e.g., prescription drugs) taken at regular intervals. The intervals of each pharmaceutical may not line up and can involve pharmaceuticals taken at intervals during a day and/or during a week. This can result in a complex pharmaceutical treatment regime, where different pharmaceuticals are taken at different times of the day and/or different days of the week. For example, in one day, a patient may take two different types of pharmaceuticals in the morning, another different type of pharmaceutical at lunch, and two additional pharmaceuticals (one of which can be the same as one taken in the morning) in the evening. The next day, the patient may either repeat the same regime, repeat some of the same regime or have an entirely different regime. Accordingly, the pharmaceutical regimen for a patient can become very complex depending on the number, types, and timing of the pharmaceuticals in the regimen and each patient may have a unique pharmaceutical regimen. Moreover, the efficacy of the pharmaceutical treatment may require relatively consistent compliance to the pharmaceutical regimen. That is, the efficacy of the treatment may require that the patient generally follow the pharmaceutical regimen, in terms of consistently undertaking the prescribed pharmaceutical in manner and at the times specified by the pharmaceutical regimen.

The treatment of some diseases or ailments may utilize relatively complex treatment regimens that may involve multiple treatments. The treatments may include medications (e.g., pharmaceuticals) of various types and administration timing. For example, some pharmaceutical regimens utilize multiple different pharmaceuticals taken orally at different time intervals and over different time periods. As mentioned above, the efficacy of the pharmaceutical treatment may require relatively consistent compliance to the pharmaceutical regimen. In this embodiment, the pharmaceutical order processing systems of the present disclosure are used to package the pharmaceuticals by pharmaceutical dose, such that each pharmaceutical dose is separately contained (e.g., dose-based filling). Each pharmaceutical dose comprises one or more pharmaceuticals (broadly, group or set of pharmaceuticals) of the pharmaceutical order/treatment regimen that are taken together at the same time. Typically, a pharmaceutical dose will include between 2-6 different pharmaceuticals. The pharmaceutical order processing systems of the present disclosure place each pharmaceutical dose in a pharmaceutical container, such as a pharmaceutical dose container. A pharmaceutical dose container holds a single pharmaceutical dose (e.g., the one or more pharmaceuticals taken at the same time) of the treatment regimen. Pharmaceutical containers can include pill bottles, cups, blister packs, and any other suitable device. In this embodiment, the pharmaceutical order processing systems fills the necessary number of pharmaceutical dose containers with the number of pharmaceutical doses in the prescription order (the number of pharmaceutical dose containers corresponding to the number of pharmaceutical doses). This organizes the pharmaceuticals in the pharmaceutical order into the pharmaceutical doses over the course of the treatment. The pharmaceutical dose containers may be prepared for different dosage times (e.g., Tuesday morning, Friday evening, etc.) and can organize the pharmaceutical regimen over a long time period, e.g., one or more weeks. For example, each pharmaceutical dose container (specifically, the pharmaceutical dose contained therein) corresponds to a time period (e.g., time of day and day of the week), such as Monday morning, for the patient to take one more pharmaceuticals of the pharmaceutical regimen. The pharmaceuticals can be the same or different for the pharmaceutical doses and pharmaceutical doses can have the same or different quantities of pharmaceuticals, with the exact makeup of the one or more pharmaceuticals in the pharmaceutical does being based on the prescribed pharmaceutical regimen. Accordingly, the organization and placement of the different pharmaceuticals in the pharmaceutical dose containers is based on the pharmaceutical regimen of the patient. The pharmaceuticals contained in pharmaceutical dose container may have a different amount relative to the another pharmaceutical dose container and/or the pharmaceuticals contained in one pharmaceutical dose container may include one or more additional pharmaceuticals not included in another pharmaceutical dose container and/or the pharmaceuticals contained in one pharmaceutical dose container may be the same as another pharmaceutical dose container.

Examples of pharmacy systems and methods can be found in U.S. Pat. No. 11,424,016, titled "PRODUCT ORDER DOSING FILLER SYSTEMS AND RELATED METHODS", filed on 14 Aug. 2019, which is hereby incorporated by reference.

Figures 3A, 3B:
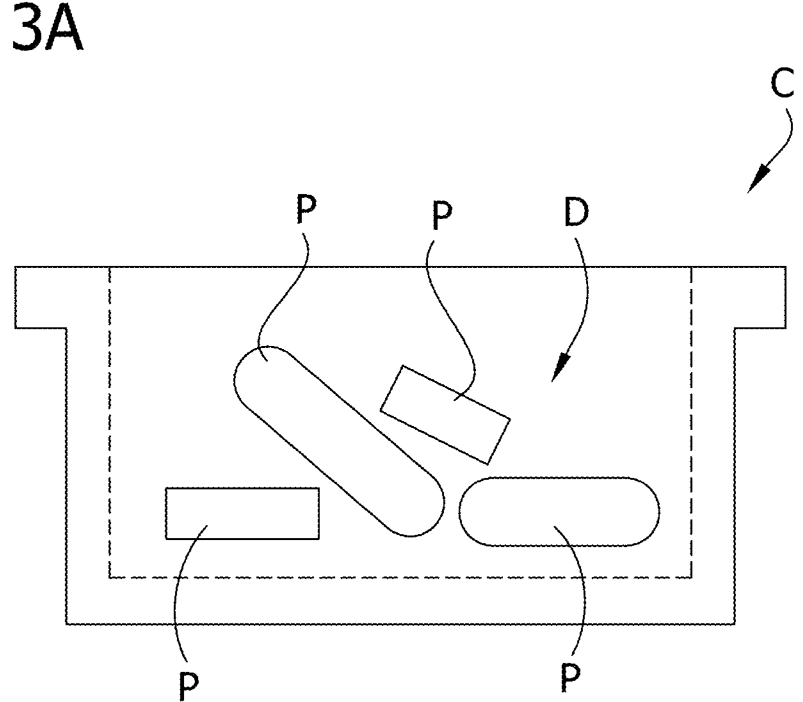
FIGS. 3A & B are elevations of a pharmaceutical container according to one embodiment of the present disclosure.

Referring to FIG. 1, one embodiment of a pharmaceutical order processing system ("system") of the present disclosure is generally indicated by reference numeral 10. In this embodiment, the system 10 is a pharmaceutical dosing filler system for filling pharmaceutical containers C (e.g., pharmaceutical dose containers) with the pharmaceutical doses D of the pharmaceutical order (FIG. 3A). The system 10 is used to create individually packaged pharmaceutical containers C of pharmaceuticals P of a single type or of multiple different types so that they may be conveniently taken by a person to whom the pharmaceuticals have been prescribed. The pharmaceuticals P may be conveniently dispensed and packaged in a pharmaceutical dose container C with other prescription drugs, vitamins, other ingestibles, and/or the like. As mentioned above, the pharmaceuticals P (and other products) contained within each pharmaceutical dose container C are associated with a time and/or a day to reduce the chances of a patient forgetting to take their medications. For example, all of the pharmaceuticals P to be consumed at a single dosing event (e.g., Monday morning) are be packaged in a single pharmaceutical dose container C. Each pharmaceutical dose D is contained within its own unique pharmaceutical dose container C.

In the illustrated embodiment, the system 10 includes an order processing device 12, a pharmaceutical dispensing device 14, a container transporter 16, a pharmaceutical inspector 18, a container sealer 20, a container former 22, and a packager 24. The system 10 can include some or all of these components and can include other components as well.

The order processing device 12 is configured to receive pharmaceuticals orders (e.g., one or more pharmaceutical orders). The order processing device 12 may receive information about the prescription orders to be filled by the system 10 and may generally control the operation of one or more of the other components of the system to fill the pharmaceutical orders. The order processing device 12 can include a controller (broadly, a computer) for controlling the operation of the system 10. In the illustrated embodiment, the controller is a dedicated controller for the system 10 and may be in communication with other components of the system. In other embodiments, the controller may be an existing controller of one of the components of the pharmaceutical order processing system. The controller controls and operates the components (e.g., the pharmaceutical dispensing device 14, the container transporter 16, the pharmaceutical inspector 18, the container sealer 20, the container former 22, and the packager 24) of the system 10. The controller has control circuitry which includes a CPU or processor 26 (e.g., a pharmaceutical order processor) and RAM or memory 28 (broadly, non-transitory computer readable storage medium). Broadly, the memory 28 includes (e.g., stores) processor-executable instructions for controlling the operation of the system 10 and the components thereof. The instructions embody one or more of the functional aspects of the system 10 and the components thereof (as described herein), with the processor 26 executing the instructions to perform said one or more functional aspects. The components of the system 10 may be in wired or wireless communication with the order processing device 12. The order processing device 12 may be embodied in a tablet, a laptop computer, a desktop computer, a mobile electronic device, and the like. Other configurations of the order processing device are within the scope of the present disclosure.

The order processing device 12 is configured (e.g. programed) to determine a container volume for containing the one or more pharmaceuticals P of each pharmaceutical dose D (broadly, at least a portion of the one or more pharmaceuticals) of the pharmaceutical order. The order processing device 12 is configured to determine the container volume based on the one or more pharmaceuticals P. Specifically, the order processing device 12 determines the container volume based on one or more characteristics of the one or more pharmaceuticals P that will be placed in the same pharmaceutical container C. The characteristics of the one or more pharmaceuticals P can include at least one of a size of each pharmaceutical, a shape of each pharmaceutical, a stacking characteristic of each pharmaceutical, or any combination thereof. The use of other characteristics, such as characteristics (e.g., size (e.g., footprint size), shape, etc.) of the pharmaceutical container C, for determining the container volume are also within the scope of the present disclosure.

Figure 2:
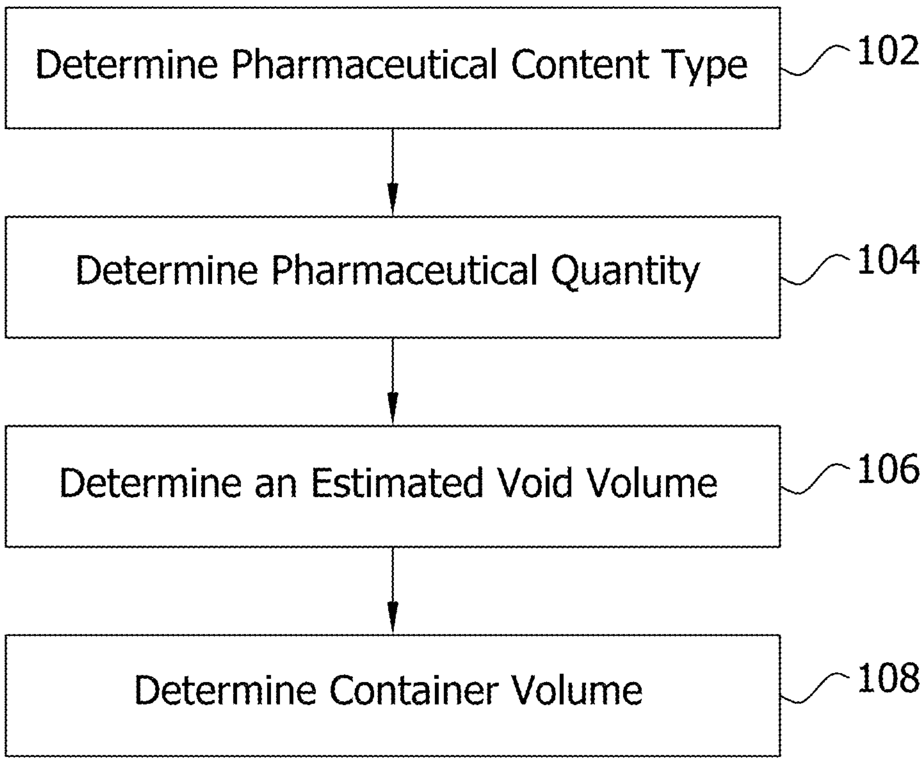
FIG. 2 is a flow diagram for determining a container volume according to one embodiment of the present disclosure.

Referring to FIG. 2, one method for determining the container volume for the pharmaceutical dose D according to the present disclosure is generally indicated at 100. This method is preferably performed by the order processing device 12. At 102, the pharmaceutical content type of the pharmaceutical dose D is determined. The pharmaceutical content type includes the types of pharmaceuticals P that are part of the pharmaceutical dose D. This information can include the size (e.g., volume) and shape of each pharmaceutical type (e.g., the size and shape of each pill for each pharmaceutical type). The size and shape of the pharmaceutical types are inputs to determine the container volume. At 104, the pharmaceutical quantity is determined. Specifically, the quantity (e.g., 1, 2, 3, etc.) for each type of pharmaceutical P of the pharmaceutical dose D is determined. For example, a pharmaceutical dose D may include two type A pharmaceuticals and two type B pharmaceuticals. In one embodiment, the pharmaceutical content type and the pharmaceutical quantity is determined by the order processing device 12. For example, the order processing device 12 may receive a pharmaceutical order containing information about the pharmaceuticals P and the rules for administering the pharmaceuticals (e.g., when each type of pharmaceutical is to be taken and the quantity of each pharmaceutical to be taken at any given time) and may determine the make-up of each pharmaceuticals dose D (e.g., the pharmaceutical content type and the pharmaceutical quantity of each pharmaceutical dose) of the pharmaceutical order based on this information. In another embodiment, the pharmaceutical content type and the pharmaceutical quantity is contained within the pharmaceutical order provided to the order processing device 12.

At 106, an estimated void volume for the pharmaceutical dose D is determined. The estimated void volume is the estimated total amount of the negative space that will be between the pharmaceuticals P when in the pharmaceutical container C (see FIG. 3A). This is based on the stacking characteristics of the one or more pharmaceuticals P. The pharmaceuticals P are going to stack in an unorganized, random manner within the pharmaceutical container C. This leaves a certain amount of void space between the pharmaceuticals P that needs to be accounted for. In one embodiment, the stacking characteristic represents an expected void volume for a particular type of pharmaceutical P based on how that particular type of pharmaceutical typically stacks with pharmaceuticals of its own type. In one embodiment, the stacking characteristic represents an expected void volume for a particular type of pharmaceutical P based on how that particular type of pharmaceutical typically stacks with pharmaceuticals of other types (e.g., pharmaceuticals having other sizes and/or shapes). In one embodiment, the order in which the different types of pharmaceuticals is used in the determination of the void volume. In one embodiment, the estimated void volume is determined by adding up all the expected void volumes for each individual pharmaceutical P of the pharmaceutical dose D. Other ways of determining the estimated void volume are within the scope of the present disclosure.

At 108, the container volume is determined based on the pharmaceutical content type, the pharmaceutical quantity, and the estimated void volume. The container volume represents the volume the pharmaceutical container C needs in order to contain all the pharmaceuticals P in the pharmaceutical dose D. In one embodiment, the container volume may include a safety factor, such as 10%, 15%, 20%, to ensure the pharmaceutical container C will be able to contain the one or more pharmaceuticals. The safety factor is generally a multiplier (e.g., 1.1 for 10%, 1.15 for 15%, 1.20 for 20%) applied before the final container volume is determined to increase the final container volume. For example, a preliminary volume can be determined based on the pharmaceutical content type, the pharmaceutical quantity, and the estimated void volume and then the safety factor is applied to the preliminary volume to get the container volume. Other ways of determining the container volume are within the scope of the present disclosure. Further details on determining the expected volume pharmaceuticals will occupy in a pharmaceutical container may be found in U.S. Pat. No. 10,947,012, the entirety of which is hereby incorporated by reference.

Referring back to FIG. 1, the container former 22 of the system 10 is in communication with (e.g., communicatively coupled to) the order processing device 12. The container former 22 is configured to form the pharmaceutical container C (e.g., pharmaceutical dose container) based on the determined container volume. This way, the formed pharmaceutical container C has the determined container volume. The container former 22 enables the system 10 to customize the pharmaceutical container C for each pharmaceutical dose D. This allows each pharmaceutical container C to be sized and/or shaped to contain the specific pharmaceutical dose D the container will contain. This minimizes the amount of material needed to form each pharmaceutical container C, keeping material costs down and minimizing manufacturing time. Further, making each pharmaceutical container C no larger than necessary minimizes the total weight of the pharmaceutical order, reducing shipping costs due to weight saving or volume reduction. In one embodiment, the container former 22 receives the container volume from the order processing device 12 and determines the size and/or shape of the pharmaceutical container C to be formed based on the container volume. For example, in one embodiment, the container former can be set to form a pharmaceutical container C having a constant footprint size and varies the height of the formed pharmaceutical container based on the container volume. In an embodiment, the container former varies the angle of the upright wall relative to the base to further adjust the interior volume. In another embodiment, the order processing device 12 determines the size and/or shape of the pharmaceutical container C to be formed based on the container volume and sends instructions to the container former 22 to form the determined pharmaceutical container.

In one embodiment, the container former 22 forms the pharmaceutical container C using additive manufacturing. In this embodiment, the container former 22 comprises an additive manufacturing machine 32, such as a 3-dimensional ("3D") printer, for forming the pharmaceutical container C, although other additive manufacturing machines and techniques are within the scope of the present disclosure. The 3D printer generally lays down successive layers of material (e.g., plastic) on top of one another to create the pharmaceutical container C. The 3D printer can form the pharmaceutical container C with generally any size and shape. In one embodiment, the additive manufacturing machine 32 is configured to form a patient label 30 (FIG. 3*b*) on the pharmaceutical container C. For example, while the additive manufacturing machine 32 is forming the body of the pharmaceutical container C, the additive manufacturing machine can also form (via additive manufacturing) the patient label 30 on the body. In one embodiment, the additive manufacturing machine utilizes different additives for coloring the patient label 30. For example, the additive manufacturing machine may apply one or more additives to the material (e.g., plastic) forming the patient label to turn the material forming the patient label into one or more colors different than the rest of the pharmaceutical container C. The patient label 30 may include at least one of a patient name 30A, a day indicia 30B, a day time indicia 30C, a prescription number 30D, pharmaceuticals name(s) 30E, or any combination thereof. The patient label may include other information as well. For example, the patient label can include the size (e.g., 100 mg, 200 mg, etc.) of each type of pharmaceutical, the quantity of each type of pharmaceutical, and/or a machine-readable marking (e.g., barcode, QR code, etc.) representing an identifier (e.g., serial number) used to identify the pharmaceutical container. The patient name 30A is the name of the patient according to the pharmaceutical order. The day indicia 30B indicates a day the pharmaceutical dose D (e.g., the one or more pharmaceuticals P) contained within the pharmaceutical container C is to be taken. In the illustrated embodiment, the day indicia 20A is an abbreviation for a day of the week (e.g., Mon. for Monday, Tu. for Tuesday, Wed. for Wednesday, Th. for Thursday, Fri. for Friday, Sa for Saturday, and Su for Sunday). In other embodiments, the day indicia may indicate the day (e.g., day 1, day 2, day 3, etc.) of the treatment regimen. The day time indicia 30C indicates the time of day the pharmaceutical dose D (e.g., the one or more pharmaceuticals P) contained within the pharmaceutical container C is to be taken. In the illustrated embodiment, the day time indicia 30C is a word (e.g., morning, noon, afternoon, evening, etc.) stating the time of day the pharmaceutical dose D is to be taken. The pharmaceutical name(s) 30E include the one or more names of the one or more pharmaceuticals P contained in the pharmaceutical container C. In one embodiment, the additive manufacturing machine 32 may form the components of the patient label 30 using a material having a different color than the material used to form the body of the pharmaceutical container C.

In one embodiment, the system 10 includes a labeling device 34 for applying the patient label 30 to the pharmaceutical container C formed by the additive manufacturing machine 32. In this embodiment, the additive manufacturing machine 32 does not form the patient label 30. In one embodiment, the labeling device 34 comprising a laser labeler, such as a laser marker, a laser etcher, a laser engraver, or the like, that forms the patient label 30 on the pharmaceutical container C. The laser labeler may color the patient label 30. In another embodiment, the labeling device 34 comprises a conventional adhesive or sticker-based labeler that generates and applies a pressure-based adhesive patient label 30 to the pharmaceutical container C. Other configurations of the labeling device 34 are within the scope of the present disclosure. The labeling device 34 applies the patient label after the pharmaceutical container C is formed by the container former 22. Accordingly, the labeling device 34 is arranged downstream of the container former 22. In the illustrated embodiment, the labeling device 34 is downstream of the pharmaceutical dispensing device 14, although other arrangements (e.g., upstream of the pharmaceutical dispensing device, immediately downstream of the container former 22) are within the scope of the present disclosure. In some embodiments, the labeling device 34 may be part of the container former 22. In the embodiment where the system 10 includes the labeling device 34, the system 10 may also include a label inspector or imager (not shown) as part of the labeling device or downstream of the labeling device for verifying the patient label was properly applied by the labeling device. The label inspector can include a camera arranged to take an image (picture or video) of the patient label on the pharmaceutical container. Further details on label inspectors can be found in U.S. Pat. No. 11,424,016, the entirety of which is hereby incorporated by reference.

Figure 4A:
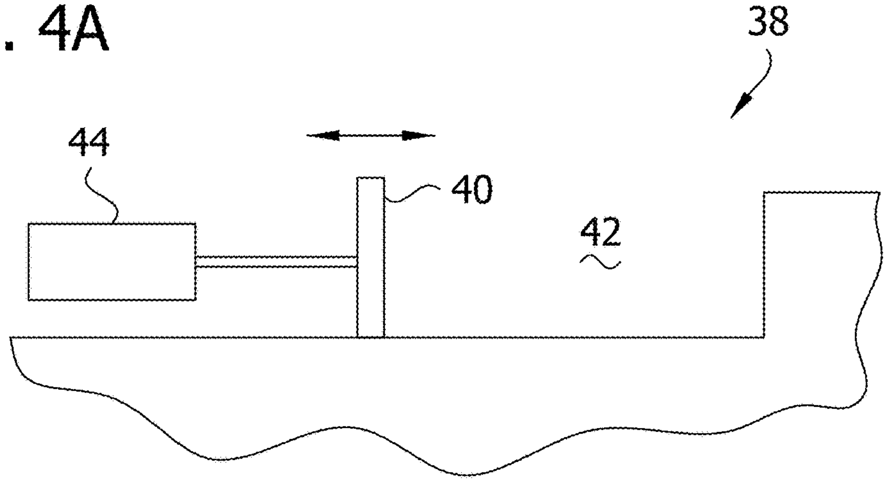
FIGS. 4A & B are elevations of different thermoforming molds according to one embodiment of the present disclosure.
Figure 4B:
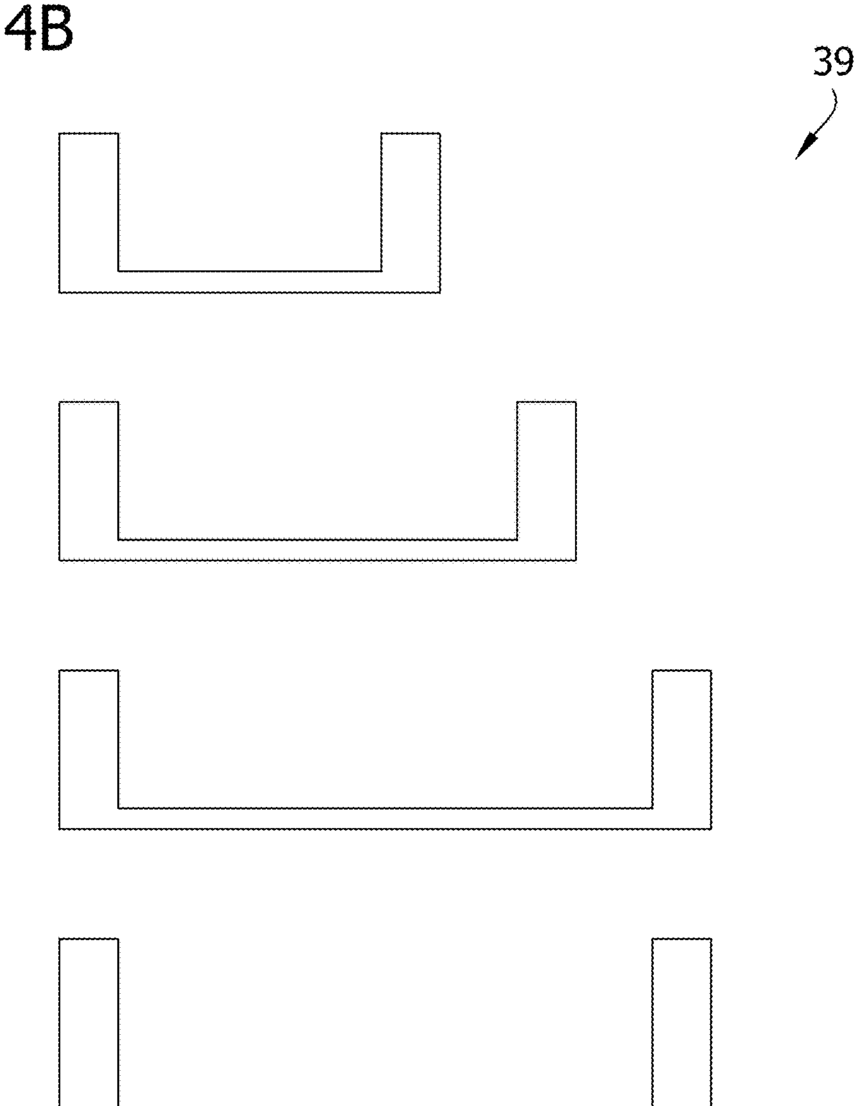

In one embodiment, the container former 22 forms the pharmaceutical container C using thermoforming. In this embodiment, the container former 22 comprises a thermoforming machine 36 for forming the pharmaceutical container C. As generally known in the art, thermoforming machines use molds to shape a softened, via heating, sheets of plastic. In this embodiment, the thermoforming machine 36 includes an adjustable pharmaceutical container mold. One example of an adjustable thermoforming mold is generally indicated at 38 in FIG. 4A. In this embodiment, the mold 38 includes a movable portion or wall 40 that is moved to adjust the size of the receiving space 42 for the thermoforming material. The movable portion 40 is operatively connected to a prime mover 44, such as an electric motor or linear actuator, which moves the movable portion based on container volume needed for the pharmaceutical container C. In another example of an adjustable thermoforming mold, the thermoforming machine may include a plurality of preset pharmaceutical container molds 39 (FIG. 4B) of different sizes and/or shapes for forming different sizes and/or shapes of pharmaceutical containers C. In this embodiment, the thermoforming machine 36 may select and use one of the preset molds 39 of the plurality of preset molds for forming the pharmaceutical container C based on the determined container volume. For example, the thermoforming machine may select one of the preset molds 39 based on the desired pharmaceutical container C shape and/or that forms pharmaceutical containers with a volume that is closest to (without going under) the determined container volume. Other configurations of the adjustable pharmaceutical container mold are within the scope of the present disclosure. In this embodiment, the system 10 may include the labeling device 34 for applying a patient label 30 to the pharmaceutical container C formed by the thermoforming machine 36, as described herein.

In one embodiment, the system 10 may include two or more container formers 22. The container formers 22 can all be the same or different. For example, all of the container formers 22 can comprise the additive manufacturing machine 32, all of the container formers can comprise the thermoforming machine 36, or one portion of the container formers can comprise the additive manufacturing machine while another portion of the container formers comprises the thermoforming machine.

The container transporter 16 is arranged to move or transport the pharmaceutical container C to and from the different components of the system 10. For example, the container transporter 16 is arranged to transport the pharmaceutical container C from the pharmaceutical dispensing device 14 toward (e.g., to) the container sealer 20. In the illustrated embodiment, the container transporter 16 receives the pharmaceutical container C after the container is formed by the container former 22 and moves the pharmaceutical container to the pharmaceutical dispensing device 14, to the labeling device 34 (if present), to the pharmaceutical inspector 18, to the container sealer 20, and then to the packager 24. In one embodiment, the container transporter 16 forms a substantially continuous loop. In one embodiment, the container transport 16 comprises a conveyor. The pharmaceutical container C may be placed directly on the conveyor or the system 10 may include container receptacles that are moved by the conveyor and receive one or more pharmaceutical containers. In one embodiment, the container transporter 16 comprises a precision mover such as MagneMotion (Rockwell Automation) or Montrac®. In one embodiment, the system 10 includes a container holding area, a container transfer device, and a container loading station. In this embodiment, the pharmaceutical containers C formed by the container former 22 are stored or held in the container holding area until the system 10 is ready to fill them with the pharmaceuticals P. The container transfer device is configured to transfer the pharmaceutical containers C from the container holding area to the container loading station, where the pharmaceutical containers are loaded onto the container transporter 16. For example, where the system 10 includes the thermoforming machine 36 with the preset molds, the thermoforming machine may make several batches of pharmaceutical containers C using each preset mold. These batches can then be stored at the container holding area. The container transfer device can select the appropriate pharmaceutical container C from container holding area based on the determined container volume and transfer the selected pharmaceutical container to the container loading station. In one embodiment, the container former 22 may feed the pharmaceutical containers C directly to the pharmaceutical dispensing device 14. In this embodiment, the container transporter 16 may receive the pharmaceutical container C from the pharmaceutical dispensing device 14.

Referring to FIG. 1, the pharmaceutical dispensing device 14 (e.g., dosing device) is configured to dispense the one or more pharmaceuticals P of the pharmaceutical dose D (broadly, at least a portion of the one or more pharmaceuticals) of the pharmaceutical order into the pharmaceutical container C formed by the container former 22. The pharmaceutical dispensing device 14 is communicatively coupled to the order processing device 12. The pharmaceutical dispensing device 14 receives information from the order processing device 12 indicating which one or more pharmaceuticals P are to be dispensed to each pharmaceutical container C. The pharmaceutical dispensing device 14 facilities the dispensing of multiple different type of pharmaceuticals P into individual pharmaceutical containers C. In one embodiment, the pharmaceutical dispensing device 14 includes a plurality of pharmaceutical counters 46. Each pharmaceutical counter 46 is configured to count and dispense (e.g., release) the precise or exact quantities (e.g., number) of pharmaceuticals P needed to fill each respective pharmaceutical container C required by the prescription order. Typically, each pharmaceutical counter 46 dispenses one type of pharmaceutical P. The pharmaceutical dispensing device 14 preferably includes a pharmaceutical stager 48 downstream of the pharmaceutical counters 46. The pharmaceutical stager 48 receives and gathers the pharmaceuticals P released by the pharmaceutical counters 46. The pharmaceutical stager 48 also dispenses or releases the gathered pharmaceuticals P to the pharmaceutical container C when the pharmaceutical container is in a position to receive the pharmaceuticals. The pharmaceutical stager 48 allows the pharmaceutical dispensing device 14 to organize a plurality of pharmaceutical doses D at once, and then individually dispense each pharmaceutical dose to its respective pharmaceutical container C. This speeds up the dispensing of the pharmaceutical dispensing device 14, enabling the pharmaceutical dispensing device to dispense more pharmaceuticals P in a given period of time. In one embodiment, the pharmaceutical stager 48 includes a plurality of buffer tubes, a plurality of funnels, a plurality of dispensing tubes, a plurality of drop tubes, a plurality of gates, and a plurality of selectively positionable guides for directing and gathering the pharmaceuticals P from the pharmaceutical counters. Further details on the pharmaceutical dispensing device 14, including the pharmaceutical counters 46 and the pharmaceutical stager 48, may be found in U.S. Pat. No. 9,697,335, the entirety of which is hereby incorporated by reference.

After the pharmaceutical dispensing device 14 fills the pharmaceutical container C with the pharmaceuticals P of the pharmaceutical dose D, the pharmaceuticals are checked by the pharmaceutical inspector 18. The pharmaceutical inspector 18 is used to verify that the correct pharmaceuticals P are in the pharmaceutical container C. The pharmaceutical inspector 18 can be an imager having a camera to arranged to take an image (e.g., picture or video) of the pharmaceuticals P in the pharmaceutical container C. The pharmaceutical inspector 18 may use color, size and/or shape of the pharmaceuticals P to verify the correct pharmaceuticals are in the pharmaceutical container. In one embodiment, instead of or in addition to the camera, the pharmaceutical inspector 18 includes an ultrasonic sensor arranged for ultrasonic imaging of the pharmaceuticals P in the pharmaceutical container C for verifying the contents of the container. Further details on pharmaceutical inspectors can be found in U.S. Pat. No. 10,151,735, the entirety of which is hereby incorporated by reference.

After the inspection by the pharmaceutical inspector 18, the pharmaceutical container C is closed or sealed by the container sealer 20. The container sealer 20 is configured to close or seal each pharmaceutical container C. This retains the one or more pharmaceuticals P of the pharmaceutical dose D in the pharmaceutical container C. In one embodiment, the container sealer 20 applies a lid or cap (e.g., a snap-on lid or cap) to each pharmaceutical container C. In one embodiment, the container sealer 20 applies a film to each pharmaceutical container C to form a seal (broadly, a thermoformed seal). Other ways of sealing the pharmaceutical containers C are within the scope of the present disclosure. In one embodiment, the container sealer 20 seals a group of pharmaceutical containers C at the same time. For example, a plurality of pharmaceutical containers C forming at least a portion of a prescription order can be grouped together and then sealed at generally the same time. The sealing may also generally join all the pharmaceutical containers C of the group together, such as one piece of film is used to seal and join all the containers. The pharmaceutical containers C can be grouped in sets, such as sets of 14, 28, 60, or 90 to correspond to different lengths of the treatment regimen (e.g., two weeks, four weeks, two months, three months respectively). The pharmaceutical containers C can also be grouped by periods of time, such as a week—e.g., every pharmaceutical container containing a pharmaceutical dose D for one week of the treatment regime is grouped together.

After the pharmaceutical container C is sealed, the pharmaceutical container is packaged by the packager 24. The packager 24 is configured to package the pharmaceutical container C for delivery, such as by packing the pharmaceutical container in a package, bag or other suitable shipping receptacle. Preferably, the packager 24 packages all the pharmaceutical containers C associated with a pharmaceutical order in one package. The packager 24 can be any suitable device for bagging, packaging, sealing, boxing, etc., the pharmaceutical containers C for shipping the containers to the patient. The packager 24 generally prepares the pharmaceutical containers C for shipping to the patient. The packager 24 may include a printer for printing a shipping label and a label applicator for applying the shipping label to the package. The package is then shipped to the patient.

Further details the system 10 (e.g., order dosing filler system), and some of its components such as the pharmaceutical order processing device 12, the container transporter 16, container receptacles, container holding area, container transfer device, container loading station, pharmaceutical dispensing device 14, pharmaceutical containers C, pharmaceutical inspector 18, container sealer 20, the packager 24 may be found in U.S. Pat. No. 11,424,016, the entirety of which is incorporated by reference into this disclosure.

In one embodiment, the system 10 is implemented in a high-volume pharmacy. In this embodiment, the system 10 may occupy one or more rooms of the high-volume pharmacy. In another embodiment, the system 10 is housed in a self-contained unit. The self-contained unit may be placed in a room of a pharmacy, such as a corner-drug store pharmacy.

Figure 5:
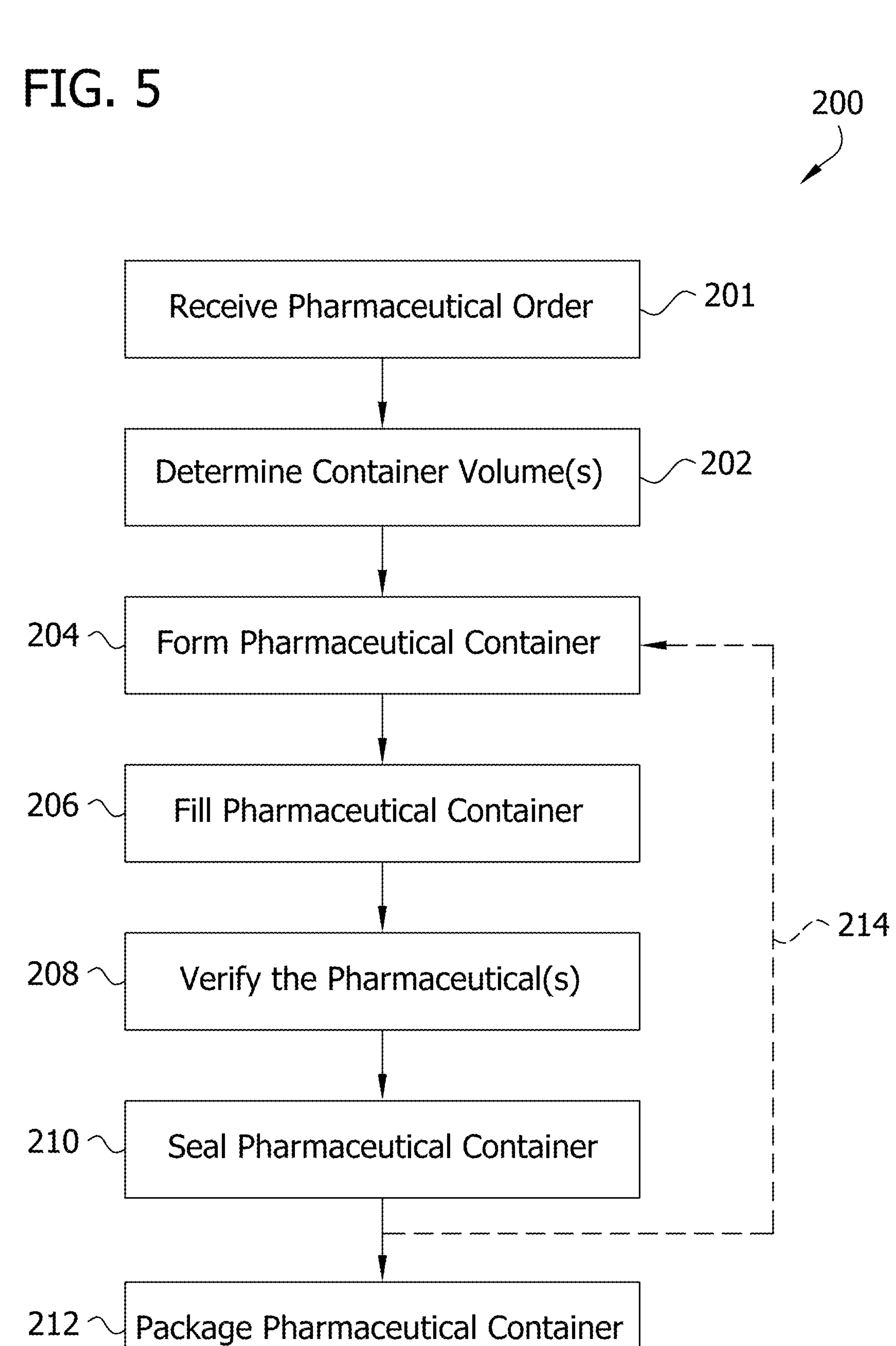
FIG. 5 is a flow diagram for filling a pharmaceutical order according to one embodiment of the present disclosure.

Referring to FIG. 5, one method for filling a pharmaceutical order using the system 10 according to the present disclosure is generally indicated at 200. At 201, the order processing device 12 receives a prescription order. If needed, the order processing device 12 determines the different pharmaceutical doses D of the pharmaceutical order, as described above. At 202, the order processing system 12 determines the container volume for each pharmaceutical container C needed for the pharmaceutical order (see FIG. 2). For example, the order processing system 12 determines the container volume for each pharmaceutical dose D of the pharmaceutical order. At 204, the container former 22 forms the pharmaceutical container C (e.g., a first pharmaceutical container) having the determined container volume (e.g., first container volume). At 206, the pharmaceutical container is filled with the one or more pharmaceuticals P (e.g., a first portion of the pharmaceuticals of the pharmaceutical order) of the pharmaceutical dose D (e.g., a first pharmaceutical dose) by the pharmaceutical dispensing device 14. Before or after the pharmaceutical container is filled, the patient label 30 (e.g., a first patient label) is applied to the pharmaceutical container, such as by the labeling device 34 or additive manufacturing machine 32 as described herein. At 208, the pharmaceutical container C with the one or more pharmaceuticals P therein is inspected by the pharmaceutical inspector 18 to verify the correct types and quantities of the pharmaceuticals are present. At 210, the container sealer 20 seals the pharmaceutical container C. At 212, the packager 24 packages the pharmaceutical container C for shipping. At 214, steps 204-210 are repeated for each pharmaceutical dose D (e.g., second, third, etc.) of the pharmaceutical order. For example, the container former 22 forms a second pharmaceutical container C having a second determined container volume. The second pharmaceutical container C is filled with the second pharmaceutical dose of the pharmaceutical order by the pharmaceutical dispensing device 14. The second pharmaceutical container C is inspected by the pharmaceutical inspector 18 and then sealed by the container sealer 20. After each pharmaceutical dose D of the pharmaceutical order is contained in a pharmaceutical container C, all the pharmaceutical containers for the pharmaceutical order can be packaged together by the packager 24, at 212, before being shipped to the patient.

The description of the operation of the system 10 above relates to the system operating as a pharmaceutical dosing filler systems for filling pharmaceuticals orders with pharmaceuticals P grouped into pharmaceutical doses D of a multi-drug treatment regimens (e.g., dose-based filling). In other embodiments, the system 10 may operate such that each pharmaceutical container C receives all of one type of pharmaceutical P of the pharmaceutical order (e.g., type-based filling). For example, if the pharmaceutical order requires a quantity of 60 pharmaceuticals of one type for the entire treatment regimen, all 60 pharmaceuticals are placed in one pharmaceutical container. This method of operation is generally the same as the method of operation described for the pharmaceutical dose base filling. For example, consider a pharmaceutical order that requires a quantity of 60 pharmaceuticals P of one type. In this example, the container volume is determined based on the total quantity (e.g., 60) of the one type of pharmaceutical P (generally, all of the one or more pharmaceuticals) because all the pharmaceuticals will be contained within one pharmaceutical container C. The container former 22 forms the pharmaceutical container C based on the container volume for all the pharmaceuticals P and the pharmaceutical dispensing device 14 dispenses all of the pharmaceuticals into the one pharmaceutical container. It is understood the system 10 may operate under either filling method (e.g., dose-based or type-based) and can perform either filling method at the same time.

In an example embodiment, the container former may three-dimensionally print edible containers. The container former as used herein may use the devices and methods set forth in U.S. patent application Ser. No. 18/131,394, filed 6 Apr. 2023, and titled EDIBLE RECEPTACLE FOR PHARMACEUTICALS; this application is hereby incorporated by reference.

Although described in connection with an exemplary computing system environment, embodiments of the aspects of the disclosure are operational with numerous other general purpose or special purpose computing system environments or configurations. The computing system environment is not intended to suggest any limitation as to the scope of use or functionality of any aspect of the disclosure. Moreover, the computing system environment should not be interpreted as having any dependency or requirement relating to any one or combination of components illustrated in the exemplary operating environment. Examples of well-known computing systems, environments, and/or configurations that may be suitable for use with aspects of the disclosure include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the aspects of the disclosure may be described in the general context of data and/or processor-executable instructions, such as program modules, stored one or more tangible, non-transitory storage media and executed by one or more processors or other devices. Generally, program modules include, but are not limited to, routines, programs, objects, components, and data structures that perform particular tasks or implement particular abstract data types. Aspects of the disclosure may also be practiced in distributed computing environments where tasks are performed by remote processing devices that are linked through a communications network. In a distributed computing environment, program modules may be located in both local and remote storage media including memory storage devices.

In operation, processors, computers and/or servers may execute the processor-executable instructions (e.g., software, firmware, and/or hardware) such as those illustrated herein to implement aspects of the disclosure.

Embodiments of the aspects of the disclosure may be implemented with processor-executable instructions. The processor-executable instructions may be organized into one or more processor-executable components or modules on a tangible processor readable storage medium. Aspects of the disclosure may be implemented with any number and organization of such components or modules. For example, aspects of the disclosure are not limited to the specific processor-executable instructions or the specific components or modules illustrated in the figures and described herein. Other embodiments of the aspects of the disclosure may include different processor-executable instructions or components having more or less functionality than illustrated and described herein.

The order of execution or performance of the operations in embodiments of the aspects of the disclosure illustrated and described herein is not essential, unless otherwise specified. That is, the operations may be performed in any order, unless otherwise specified, and embodiments of the aspects of the disclosure may include additional or fewer operations than those disclosed herein. For example, it is contemplated that executing or performing a particular operation before, contemporaneously with, or after another operation is within the scope of aspects of the disclosure.

It is apparent that the elements, features, and/or teachings set forth in each embodiment disclosed herein are not limited to the specific embodiment(s) in which the elements, features and/or teachings are explicitly described. Accordingly, it is understood that the elements, features and/or teachings described in one embodiment may be applied to one or more of the other embodiments disclosed herein, even if said elements, features and/or teachings where not described herein as being a part of said one or more of the other embodiments.

The Title, Field, and Background are provided to help the reader quickly ascertain the nature of the technical disclosure. They are submitted with the understanding that they will not be used to interpret or limit the scope or meaning of the claims. They are provided to introduce a selection of concepts in simplified form that are further described in the Detailed Description. The Title, Field, and Background are not intended to identify key features or essential features of the claimed subject matter, nor is it intended to be used as an aid in determining the claimed subject matter.

When introducing elements of aspects of the disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the aspects of the disclosure are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the aspects of the disclosure by way of example and not by way of limitation. This description enables one skilled in the art to make and use the aspects of the disclosure, and describes several embodiments, adaptations, variations, alternatives and uses of the aspects of the disclosure, including what is presently believed to be the best mode of carrying out the aspects of the disclosure. Additionally, it is to be understood that the aspects of the disclosure is not limited in its application to the details of construction and the arrangement of components set forth in the description or illustrated in the drawings. The aspects of the disclosure are capable of other embodiments and of being practiced or carried out in various ways. Also, it will be understood that the phraseology and terminology used herein is for the purpose of description and should not be regarded as limiting.

Having described aspects of the disclosure in detail, it will be apparent that modifications and variations are possible without departing from the scope of aspects of the disclosure as defined in the appended claims. It is contemplated that various changes could be made in the above constructions, products, and methods without departing from the scope of aspects of the disclosure. In the preceding specification, various embodiments have been described with reference to the accompanying drawings. It will, however, be evident that various modifications and changes may be made thereto, and additional embodiments may be implemented, without departing from the broader scope of the aspects of the disclosure as set forth in the claims that follow. The specification and drawings are accordingly to be regarded in an illustrative rather than restrictive sense.

What is claimed is:

1. A pharmaceutical order processing system comprising:

an order processing device configured to receive a pharmaceutical order including one or more pharmaceuticals, the order processing device configured to determine a container volume for containing at least a portion of the one or more pharmaceuticals based on the one or more pharmaceuticals;

a container former communicatively coupled to the order processing device, the container former configured to form a pharmaceutical container having the container volume determined by the order processing device; and a pharmaceutical dispensing device communicatively coupled to the order processing device, the pharmaceutical dispensing device configured to dispense said at least a portion of the one or more pharmaceuticals into the pharmaceutical container formed by the container former, wherein said at least a portion of the one or more pharmaceuticals includes all of the one or more pharmaceuticals, the order processing device being configured to determine the container volume for containing said all of the one or more pharmaceuticals based on the one or more pharmaceuticals, and the pharmaceutical dispensing device configured to dispense said all of the one or more pharmaceuticals into the pharmaceutical container.

2. The pharmaceutical order processing system of claim 1, wherein the container former includes an additive manufacturing machine configured to form the pharmaceutical container.

3. The pharmaceutical order processing system of claim 2, wherein the additive manufacturing machine is configured to form a patient label on the pharmaceutical container, the patient label including at least one of a patient name, a day indicia indicating a day said at least a portion of the one or more pharmaceuticals is to be taken, a day time indicia indicating a time of day said at least a portion of the one or more pharmaceuticals is to be taken, a prescription number, one or more names of the one or more pharmaceuticals, or a combination thereof.

4. The pharmaceutical order processing system of claim 2, wherein the additive manufacturing machine comprises a 3-dimensional printer.

5. The pharmaceutical order processing system of claim 1, further comprising a laser labeler configured to form a patient label on the pharmaceutical container, the patient label including at least one of a patient name, a day indicia indicating a day said at least a portion of the one or more pharmaceuticals is to be taken, a day time indicia indicating a time of day said at least a portion of the one or more pharmaceuticals is to be taken, a prescription number, one or more names of the one or more pharmaceuticals, or a combination thereof.

6. The pharmaceutical order processing system of claim 1, wherein the container former includes a thermal forming machine.

7. The pharmaceutical order processing system of claim 6, wherein the thermal forming machine includes an adjustable pharmaceutical container mold.

8. The pharmaceutical order processing system of claim 6, wherein the thermal forming machine includes a plurality of pharmaceutical container molds of different sizes for forming different sizes of pharmaceutical containers, the thermal forming machine configured to select one of the pharmaceutical container molds for forming the pharmaceutical container based on the container volume determined by the order processing device.

9. The pharmaceutical order processing system of claim 1, wherein the order processing device is configured to determine the container volume based on one or more characteristics of the one or more pharmaceuticals, the one or more characteristics including at least one of a size of each pharmaceutical of the one or more pharmaceuticals, a shape of each pharmaceutical of the one or more pharmaceuticals, a stacking characteristic of each pharmaceutical of the one or more pharmaceuticals, a quantity of the one or more pharmaceuticals, or a combination thereof.

10. The pharmaceutical order processing system of claim 1, wherein said at least a portion of the one or more pharmaceuticals forms a pharmaceutical dose of the pharmaceutical order.

11. The pharmaceutical order processing system of claim 1, further comprising a container transporter and a container sealer, the container sealer being configured to seal the pharmaceutical container with the one or more pharmaceuticals contained therein, the container transporter arranged to transport the pharmaceutical container from the pharmaceutical dispensing device to the container sealer.

12. The pharmaceutical order processing system of claim 11, further comprising a packager configured to package the pharmaceutical container for delivery, the container transporter arranged to transport the pharmaceutical container to the packager.

13. A method of filling a pharmaceutical order including one or more pharmaceuticals, the method comprising:

determining a container volume for containing all of the one or more pharmaceuticals based on the one or more pharmaceuticals and packaging for all of the one or more pharmaceuticals;

forming a pharmaceutical container, using a container former, having the determined container volume to receive the one or more pharmaceuticals; and filling the formed pharmaceutical container with said all of the one or more pharmaceuticals using a pharmaceutical dispensing device.

14. The method of claim 13, wherein said forming the pharmaceutical container includes forming the pharmaceutical container via additive manufacturing.

15. The method of claim 13, wherein said forming the pharmaceutical container includes forming the pharmaceutical container via thermoforming.

16. The method of claim 13, further comprising forming a patient label on the pharmaceutical container via additive manufacturing, the patient label including at least one of a patient name, a day indicia indicating a day said at least a portion of the one or more pharmaceuticals is to be taken, a day time indicia indicating a time of day said at least a portion of the one or more pharmaceuticals is to be taken, a prescription number, one or more names of the one or more pharmaceuticals, or a combination thereof.

17. The method of claim 13, further comprising forming a patient label on the pharmaceutical container via a laser labeler, the patient label including at least one of a patient name, a day indicia indicating a day said at least a portion of the one or more pharmaceuticals is to be taken, a day time indicia indicating a time of day said at least a portion of the one or more pharmaceuticals is to be taken, a prescription number, one or more names of the one or more pharmaceuticals, or a combination thereof.

18. The method of claim 13, wherein said determining the container volume is based on one or more characteristics of the one or more pharmaceuticals, the one or more characteristics including at least one of a size of each pharmaceutical of the one or more pharmaceuticals, a shape of each pharmaceutical of the one or more pharmaceuticals, a stacking characteristic of each pharmaceutical of the one or more pharmaceuticals, a quantity of the one or more pharmaceuticals, or a combination thereof.

19. The method of claim 13, wherein said at least a portion of the one or more pharmaceuticals comprises is a first portion of the one or more pharmaceuticals, the container volume is a first container volume, and the pharmaceutical container is a first pharmaceutical container, the method further comprising:

determining a second container volume for containing at a second portion of the one or more pharmaceuticals based on the one or more pharmaceuticals;

forming a second pharmaceutical container having the determined second container volume; and filling the formed second pharmaceutical container with said second portion of the one or more pharmaceuticals.

20. The method of claim 19, wherein said at least a portion of the one or more pharmaceuticals comprises is a first portion of the one or more pharmaceuticals, the container volume is a first container volume, and the pharmaceutical container is a first pharmaceutical container, wherein the order processing device is configured to determine a second container volume for containing a second portion of the one or more pharmaceuticals different from the first container volume;

wherein the container former is configured to form a second pharmaceutical container having the determined second container volume; and the pharmaceutical dispensing device configured to fill the formed second pharmaceutical container with the second portion of the one or more pharmaceuticals.

* * * * *